US005244677A

United States Patent [19]

Kreckel et al.

[11] Patent Number: 5,244,677
[45] Date of Patent: Sep. 14, 1993

[54] APPLICATION SYSTEM FOR DRUG CONTAINING MICROEMULSIONS

[75] Inventors: Karl W. Kreckel; Horst-Georg Zerbe, both of Borken, Fed. Rep. of Germany

[73] Assignee: Minnesota Mining and Manufacturing Company, St. Paul, Minn.

[21] Appl. No.: 979,446

[22] Filed: Nov. 20, 1992

Related U.S. Application Data

[63] Continuation of Ser. No. 566,447, Feb. 22, 1990, abandoned.

[30] Foreign Application Priority Data

Dec. 29, 1988 [DE] Fed. Rep. of Germany ....... 3844247

[51] Int. Cl.$^5$ .............................................. A61F 13/02
[52] U.S. Cl. .................................... 424/448; 424/447; 424/449
[58] Field of Search ................ 424/448, 449, 447, 443

[56] References Cited

U.S. PATENT DOCUMENTS

| | | | |
|---|---|---|---|
| 3,328,482 | 6/1967 | Northrup et al. | 521/490 |
| 3,503,782 | 3/1970 | Ayres | 428/211 |
| 3,527,659 | 9/1970 | Keil | 428/447 |
| 3,741,786 | 6/1973 | Torrey | 428/40 |
| 4,117,841 | 10/1978 | Perrotta et al. | 424/448 |
| 4,208,504 | 6/1980 | Hockemeyer et al. | 528/15 |
| 4,397,905 | 8/1983 | Dettmer et al. | 428/180 |
| 4,592,753 | 6/1986 | Panoz | 424/448 |
| 4,597,961 | 7/1986 | Etscorn | 424/448 |
| 4,605,548 | 8/1986 | Ushiyama et al. | 424/15 |
| 4,655,768 | 4/1987 | Marecki et al. | 424/448 |
| 4,788,064 | 11/1988 | Patel et al. | 424/444 |
| 4,812,305 | 3/1989 | Vocal | 424/448 |
| 4,842,902 | 6/1989 | Brown et al. | 428/40 |
| 4,904,475 | 2/1990 | Gale et al. | 424/449 |
| 4,956,181 | 9/1990 | Bayer et al. | 424/448 |
| 4,994,049 | 2/1991 | Latzke et al. | 604/307 |
| 5,061,535 | 10/1991 | Kreckel et al. | 428/195 |

FOREIGN PATENT DOCUMENTS

| | | |
|---|---|---|
| 0117027 | 1/1984 | European Pat. Off. . |
| 0113562 | 7/1984 | European Pat. Off. . |
| 0153200A2 | 8/1985 | European Pat. Off. . |
| 885746 | 6/1949 | Fed. Rep. of Germany . |
| 3007769 | 9/1981 | Fed. Rep. of Germany . |
| 3629304A1 | 8/1986 | Fed. Rep. of Germany . |
| 3714140A1 | 4/1987 | Fed. Rep. of Germany . |
| 3727078 | 2/1989 | Fed. Rep. of Germany . |
| 963182 | 7/1964 | United Kingdom . |
| 1361289 | 6/1971 | United Kingdom . |
| 2209148 | 5/1989 | United Kingdom . |

Primary Examiner—Thurman K. Page
Assistant Examiner—Leon R. Horne
Attorney, Agent, or Firm—Gary L. Griswold; Walter N. Kirn; Douglas E. Reedich

[57] ABSTRACT

The invention deals with devices, in particular with bandage strips, for a transdermal delivery of drugs to patients, whereby the drug formulations include highly viscous preparations, topical solutions of a low viscosity and micro-emulsions of a low viscosity containing the drugs. Depending on the consistency of the medium containing the drug, the drug formulation is stored in a reservoir, consisting, e.g., of a punched out cavity or of an absorbent piece of material, which is encased or supported by a carrier element (a foamed material piece or a non-woven fleece tape) adhering to the skin by means of a skin-compatible adhesive, whereby specially formed protective films are applied at the filling and delivery side during the storage of the device to prevent a lateral migration, and whereby during its use, the device can be refilled with dosed amounts by the patient without requiring a removal of the device from the skin surface to be treated (FIG. 2).

10 Claims, 3 Drawing Sheets

APPLICATION SYSTEM FOR DRUG CONTAINING MICROEMULSIONS

This is a continuation of application Ser. No. 07/566,447 filed Feb. 22, 1990 now abandoned.

DESCRIPTION

The invention deals with a device, in particular with a bandage strip, for a transdermal delivery of a drug to a patient with a reservoir for storing and delivering the drug onto the skin of the patient and with a carrier element for carrying the reservoir, whereby this carrier element is provided with a skin-compatible adhesive layer, by which the device is adhered to the skin of the patient in the application state, and with a peelable protective film (liner) covering the adhesive layer and the reservoir at the side of delivery in the state of storage.

It has been known to orally administer drugs in the form of droplets, tablets, pills or powders. The drugs will reach the intestinal tract via the esophagus and the stomach and will be absorbed in this manner by the body. By the administered amounts, which are given several times per day in certain dosages, a drug influx is achieved each time. After the absorption in the gastrointestinal tract, the drug is passed into the liver, where in many cases, a more or less pronounced transformation into less effective metabolites takes place. This so-called "first pass effect" will be by-passed by a transdermal drug delivery, where the drug is applied on the skin and diffused through the skin directly into the blood stream, while by-passing the gastro-intestinal tract.

For the transdermal delivery of drugs, application fields for various kinds of drugs have been known. For instance, a bandage strip of the aforementioned kind (described in the laid-open European Patent Application 153 200) contains a carrier element with a central section having a cross-section of a truncated cone open at the bottom, which forms the reservoir containing the solution or suspension of the drug to be delivered. Furthermore, the carrier element is provided with a skin-compatible adhesive layer and a peelable protective film covering the adhesive layer and the opening area of the reservoir in the state of storage (see FIG. 1b in conjunction with p. 7, paragraph 1 and the summary of the said European patent application). This known bandage strip is found to be disadvantageous due to the fact, that a low-viscous medium containing the drug, will be easily spilled or be spread over the skin area, to which it is to be administered in a specific target area, while attempting to peel off the protective film and placing at the same time the bandage strip onto the skin of a patient, whereby the desired effect will not be achieved. If the solution or suspension containing the drug is diffused through the skin after the application of the bandage and if still a further amount of the solution or suspension is to be administered to the patient, the bandage has to be removed from the skin and has to be replaced by a new bandage. Furthermore, there is the danger of a leakage during storage, due to a lateral migration of the solution or suspension into the adhesive layer coated on the carrier material, resulting in an insufficient adhesion of the bandage strip during the later application.

Furthermore, a device for the transdermal delivery of an active ingredient has been known (U.S. Pat. No. 4,597,961), whereby a hollow cavity in an impermeable flexible material of poly(vinyl chloride), polypropylene, nylon or silicone rubber serves as a reservoir for a liquid formulation of an active ingredient to be transcutaneously applied. This flexible material is coated at the side of delivery with a skin-compatible adhesive layer and fitted with a protective film sealing the opening area of the hollow cavity (see FIG. 1 in conjunction with column 5, lines 7 to 21, and also the summary of U.S. Pat. No. 4,597,961). For this device, too, the disadvantages described above are experienced accordingly.

It has also been known (laid-open European patent application 113 562, page 1, paragraph 2 from the bottom) to blend a drug with an adhesive and to apply this mixture on a suitable carrier material in several layers, whereby the concentration of the drug in the adhesive is chosen in such a way, that the last applied layer, i.e. the layer directly in contact with the skin, has the lowest concentration of the drug, and that the layer the furthest away from the skin, has the highest concentration of the drug. Thereby, the reaction mechanism is determined, namely due to the highest concentration being in the layer the farthest away from the skin, the drug delivery through the skin will occur at an about uniform permeation rate.

The objectives to be achieved by the invention deal with the development of a device for a dermal delivery of a drug onto the skin of a patient according to the aforementioned kind, whereby a defined amount of a liquid preparation of a drug will be exactly fixed at a location on the skin intended for the application and to be delivered during a defined time of application, and whereby a lateral migration of the medium containing the drug will be prevented during the state of storage as well as also during the usage of the device, since this kind of migration will result in a deterioration of the adhesion to the skin. This migration needs to be particularly considered, if micro-emulsions are used as the medium containing the drug exhibiting a high surface activity and a low surface tension, whereby in particular a leakage during the storage of the device is to be prevented.

These objectives have been achieved according to the invention in regard to a delivery of highly viscous ointments, pastes or the like, whereby the carrier element is formed by a relatively flat foamed piece of material with closed pores, which is traversed between the opposite surfaces by a punched out perforating hole forming the reservoir, in which the highly viscous drug preparation (paste or ointment) is placed to be slowly diffused through the skin during the final usage of the device, and whereby a polymer film coated with an adhesive, is placed onto the surface of the foamed material piece at the side opposite the side carrying the skin-compatible adhesive layer, thereby covering the reservoir at the fill-in side, and whereby the peelable protective film consists of an adhesion releasing protective film preventing a lateral migration during the storage of the device.

Advantageous further developments of the device according to the invention are described in the patent claims 2 to 11.

For a transdermal delivery of low-viscous solutions, the device according to the invention is formed in such a way that the carrier element consists of a non-woven fleece tape with an adhesive layer applied to its bottom side, to which an element of an absorbent material forming the reservoir, is adhesively attached at the fill-in side, whereby a filling opening for at least one low-viscous drug solution is provided traversing the non-woven tape and its adhesive layer and forming a communicating connection with the absorbent element, which is saturated with the low-viscous drug solution in the state of storage of the device, and whereby the surface of the non-woven fleece tape is provided with a cover coated with a pressure-sensitive repeatedly usable adhesive layer covering the filling opening, and whereby the peelable protective film consists of an adhesion releasing protective film preventing a lateral migration during the storage of the device.

Advantageous further developments of this device according to the invention are described in the patent claims 13 to 23.

The device according to the invention may be suitably used for a repeated dosed delivery of media with a high viscosity or of solutions with a low viscosity onto the skin area of a patient without requiring a removal of the device. Thereby, a particularly easily manageable and effective treatment of the patient is possible.

For a transdermal delivery of low-viscous micro-emulsions containing the drugs, the device according to the invention is formed as follows: The carrier element consists of a relatively flat foamed material piece with closed pores, on which a hot-melt adhesive layer is placed at the side opposite the side containing the skin-compatible adhesive layer, and whereby the composite structure consisting of the adhesive layer, the foamed material and the skin-compatible adhesive layer, is traversed by a punched out perforating hole, in which an absorbent material is placed absorbing the micro-emulsion containing the drug, and whereby a protective film is attached to the adhesive layer at the filling side covering the punched out openings and, thereby, preventing a lateral migration of the micro-emulsion adsorbed at the absorbent material and containing the drug preparation, and whereby the peelable protective film (liner) is attached to the skin-compatible adhesive layer, covering and sealing the punched out opening at the delivery side during the storage of the device, and whereby the peelable protective film consists of an adhesion releasing protective film preventing a lateral migration during the storage of the device.

Advantageous further developments of this device according to the invention are described in the patent claims 25 to 33.

The selection of the adhesive in the composite structure, depends on the type of the employed foamed material. Suitable hot-melt adhesives are well known to the skilled artisan. By heat-sealing the hot-melt adhesive layer and the polyethylene film vapor coated with aluminum, a very strong bond between the foamed material piece of polyethylene and the cover film covering the reservoir is obtained effectively preventing a lateral migration of the low-viscous micro-emulsion contained in the absorbent material.

It is important that the thickness of the absorbent material contained in the punched out cavity is slightly less than the thickness of the polyethylene foam-piece for avoiding a pressing of the micro-emulsion into the interface between the pressure-sensitive adhesive and the cover (the protective layer).

The peelable protective film coated in a particular pattern with a silicone or another adhesion releasing material will provide a reliable barrier for preventing a lateral migration of the micro-emulsion between the peelable protective film and the surface of the skin-compatible adhesive layer while the device is stored.

For achieving a sufficiently long storage time of a ready-to-use bandage strip, a particular property of the peelable protective film is required, which depends on the physico-chemical properties of the liquid medium containing the drug component. The peelable protective film has to exhibit a good barrier effect against an under-migrating of the adhesive and has to be readily peelable during the application of the bandage. Due to the possibility to vary the ratio of the sizes and/or of the shapes of the coated and non-coated part-areas of the pattern on the surface of the protective film, an optimizing of a suitable barrier property and of a favorable peelability of the protective film is achievable.

Even in the cases where the properties and viscosity of the micro-emulsion will assure an extremely good diffusion through the skin of the patient, by which at the same time also the dangers of an undermigrating of the skin-compatible adhesive layer by the micro-emulsion will be extremely increased, the particularly formed protective film will prevent any kind of leakage of the micro-emulsion during the storage of the device.

Preferably, the skin-compatible adhesive may consist of components which prevent a penetration by the micro-emulsion containing the drug.

Advantageous forms of execution of the device according to the invention, by which the various viscosities of the drug formulations to be applied in a transdermal delivery system are taken into account, shall be further explained by referring to the attached drawings:

BRIEF DESCRIPTION OF THE DRAWINGS

As seen in FIG. 1 and 2, a reservoir (5) has been punched out in a foamed material piece (2) containing closed pores. The one surface of this foamed material piece (2) is provided with a skin-compatible adhesive layer (3), which in turn is covered by a siliconized protective film (4) consisting of paper or another suitable material. The protective film (4) of paper is provided with a pull-off strap (6) and covers the punched out reservoir (5) in the foamed material piece (2) during the storage of the bandage strip. As shown in FIG. 1, the reservoir (5) has a circular cross-section. As recognized in FIG. 2, the adhesive layer (3) is peripherally encasing the punched out reservoir (5).

Figure 1:
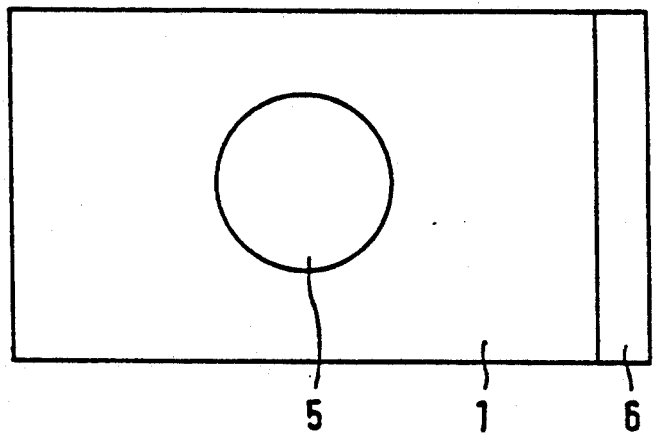
FIG. 1 illustrates a topview of a form of execution of the device for a dermal delivery of ointments or pastes, i.e. drug formulations with a high viscosity.
Figure 2:
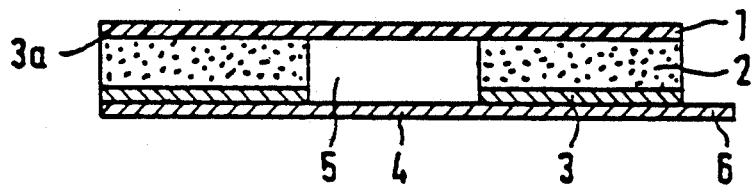
FIG. 2 is a sectional schematic layout of the form of execution shown in FIG. 1.

The opposite surface of the foamed material piece (2) is covered by a polymer film (1) by means of an adhesive (3a). This polymer film (1) may be transparent and micro-perforated and may be removably adhesively attached. The adhesive (3a) may be repeatedly usable.

This bandage strip is applied in a manner, whereby at first the protective film (4) of paper is peeled off and the bandage strip is placed onto the skin in such a way that the location of the skin to be treated is visible in the reservoir (5).

Then, the transparent polymer film (1) on the opposite surface of the foamed material piece (2) is lifted and the highly viscous drug formulation will be placed into the reservoir (5). However, the highly viscous drug formation may also already earlier be placed into the reservoir (5) in the state of storage of the bandage strip or may be placed into an open-cell foamed material piece. After the application, the drug will slowly penetrate into the skin, whereby the medicinal treatment of the patient will take place.

Figure 3:
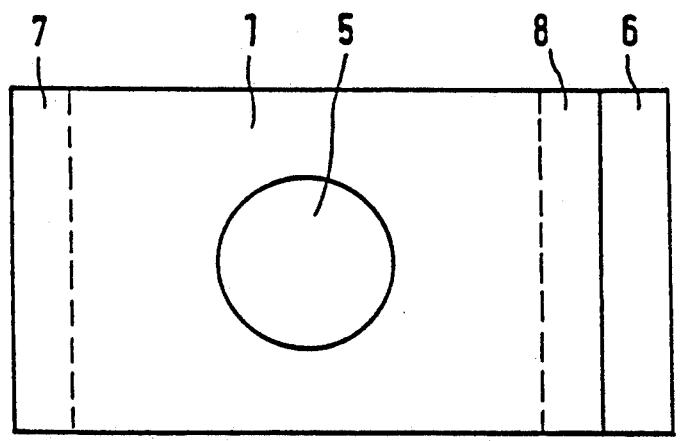
FIG. 3 illustrates a topview of another form of execution of the device for a dermal delivery of highly viscous drug formulations.
Figure 4:
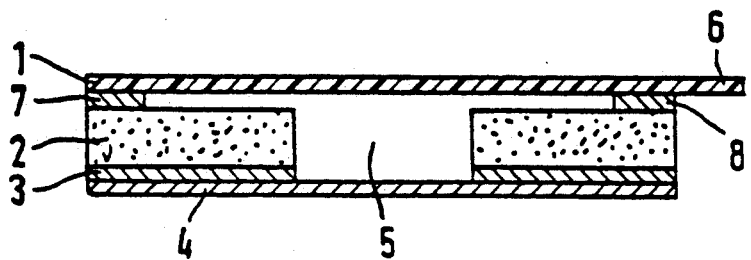
FIG. 4 is a sectional schematic layout of the form of execution shown in FIG. 3.

In FIG. 3 and 4, a modification of the earlier described form of execution is shown, where a non-transparent polymer film (cover) (1) is used and the respective adhesive layers (7) and (8) with different properties.

Opposite the pull-off strap (6), the polymer film (1) is provided along the crosswise edge with an adhesive strip (7) of an adhesive with a high adhesive strength. The adhesive strip (8) adjacent to the pull-off strap (6), is formed from a (repeatedly usable) adhesive of a lower adhesive strength. This adhesive strip (8) of an adhesive with a low adhesive strength may consist either of a relatively narrow strip adjacent the pull-off strap (6) or of a wider strip covering the area up to the strip (7). In this foamed material piece (2), the reservoir (5) has again been punched out.

EXAMPLE 1

A device according to the invention for administering a highly viscous ointment or paste, was prepared as follows:

A polyethylene foam piece with closed cells and about 1 to 2 mm thick was coated at both sides with an acrylate adhesive.

Then, holes with a diameter of e.g. 30 mm, were punched out of the coated foam piece.

A 40 μm thick polypropylene film, micro-perforated, was laminated onto one of the surfaces of the polyethylene foam piece coated with the acrylate adhesive.

Then, open-cell polyurethane foam pieces of a polyether base and with a low initial density were placed into the punched out openings.

In this polyurethane foam piece, the ointment will be placed at the later application. Then, a protective polyester film fully coated with a silicone or another adhesion releasing material was laminated on the still remaining area of the adhesive layer.

Then, the laminate was cut into individual pieces of a suitable size of, e.g., 50 mm × 60 mm.

The transdermal administration of drug formulations with a low viscosity is in part substantially more difficult, since the drug formulations can often not be retained at the location needed for the treatment. Furthermore, the concentration of a drug formulation with a low viscosity is relatively difficult to be attained on a small skin area.

Figure 5:
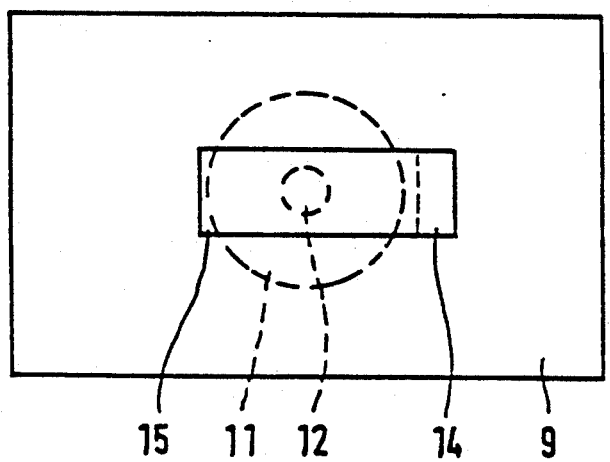
FIG. 5 illustrates a topview of a form of execution of the device for a dermal delivery of low-viscous solutions.
Figure 6:
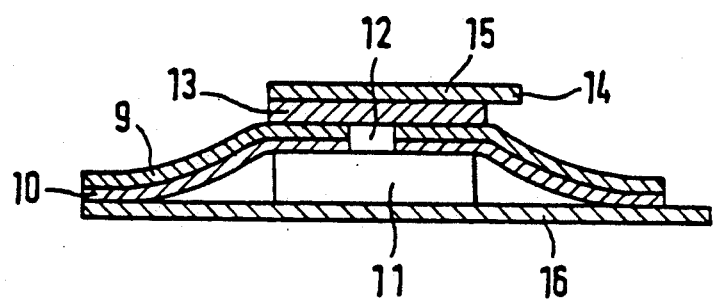
FIG. 6 is a sectional schematic layout of the form of execution shown in FIG. 5.
Figure 7:
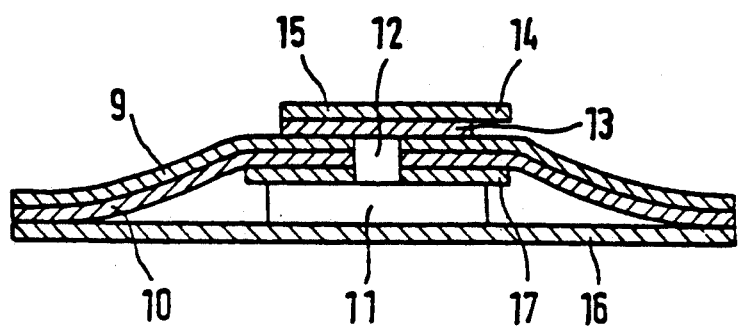
FIG. 7 is a sectional schematic layout of a modification of the form of execution shown in FIG. 5.

However, the forms of execution of the device illustrated in the FIGS. 5 to 7, advantageously permit a reliable delivery of drugs or drug formulations, respectively, with a low viscosity.

As seen in FIG. 5 and 6, an absorbent material piece (11) shaped, e.g., as a small circular disk, is held in place by a tape (9) of a non-woven fleece coated with an adhesive layer (10) and fitted with a small filling opening (12) situated above the center of the absorbent disk (11). Via the punched out filling opening (12) in the non-woven fleece tape (9) and the attached adhesive layer (10), the low-viscous drug formulation may be refilled each time as needed by lifting the cover (15) covering the filling opening (12) and by closing the cover again after the drug formulation has been filled into the disk (11) via the filling opening (12). The cover (15) is fitted with a pull-off strap (14). The dosing of the amount to be delivered, may be carried out by the patient himself. The disk (11) of an absorbent material is normally saturated with the drug solutions of a low viscosity. The cover (15) is coated with an adhesive layer (13), which is repeatedly usable. The protective film (liner) (16) is readily peelable and is situated at the delivery side of the disk (11) of an absorbent material during the storage of the bandage strip.

In FIG. 7, a modification of the form of execution shown in FIG. 5 and 6 is illustrated, where an impermeable barrier layer (17) is placed on the filling side surface of the disk (11) of the absorbent material and is traversed by the filling opening (12) reaching the disk (11) in a communicating manner. The barrier layer (17) is adhesively bonded to the skin-compatible adhesive layer (10) of the non-woven tape (9) and peripherally extends beyond the disk (11). By means of this form of execution, a penetration into or an attack of the bond between the non-woven tape (9) and the skin-compatible adhesive layer (10) by certain drug solutions is avoided.

EXAMPLE 2

A device according to the invention for administering low-viscous solutions was prepared as follows:

A medical adhesive tape consisting of a non-woven rayon fleece material coated with a skin-compatible adhesive was laminated with a disk of a polyethylene film, which was vapor-coated with aluminum and also coated with a layer of a pressure-sensitive adhesive. In this laminate, holes with a diameter of about 3 mm were punched.

A piece of a non-woven fleece of viscose rayon, about 1 mm thick was placed on the pressure-sensitive adhesive side of the aluminum vapor-coated polyethylene film. The diameter of this non-woven material piece is to be smaller than the diameter of the barrier layer film.

Then, a protective paper fully coated with a silicone or another adhesion releasing material, was laminated onto the still remaining area of the pressure-sensitive adhesive layer.

For covering the filling opening, a pull-off strap in the form of a 5 mm wide and 2 cm long adhesive tape strip was placed onto the upper side of the device.

For facilitating the peeling action, a piece of an adhesive paper was attached to the end of this pull-off strap.

Then, the entire composite structure was cut into individual pieces, about 50×60 mm in size.

Figure 9:
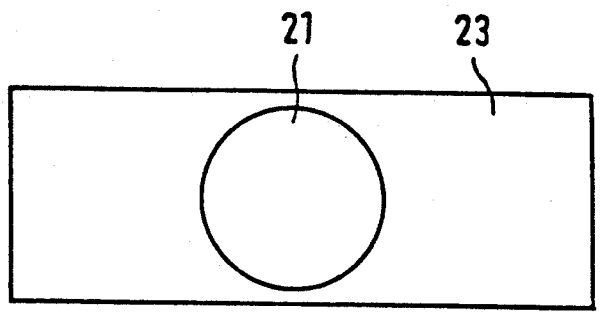
FIG. 9 illustrates a topview of the form of execution shown in FIG. 8.
Figure 8:
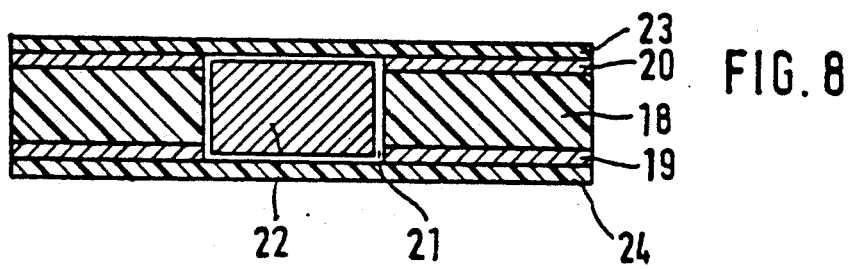
FIG. 8 is a sectional schematic layout of a form of execution of the device for a transdermal delivery of micro-emulsions containing the drugs.

In FIGS. 8 and 9, a form of execution of the device is illustrated for a transdermal delivery of low-viscous micro-emulsions containing the particular drugs. These micro-emulsions are contained in a material piece (22) of absorbent materials placed in a punched out reservoir (21) traversing the polyethylene foam piece (18) having closed cells. The thickness of the polyethylene foam piece (18) is slightly larger than the thickness of the absorbent material (22) containing adsorptively bonded the micro-emulsion of the drug to be applied, whereby a pressure equalization is possible. At the one surface of the polyethylene foam piece (18), a skin-compatible pressure-sensitive adhesive layer (19) is placed, which in turn is covered by a protective film (24) of polyester or of other suitable materials during the storage of the device.

The opposite surface side of the polyethylene foam piece (18) is preferably coated with a hot-melt adhesive layer (20) of ethylene/vinyl acetate, by which a protective polyethylene film (23), preferably vapor-coated with aluminum, is adhered. The hot-melt adhesive layer (20) and the protective polyethylene film (23) are heat-sealed with each other under the formation of a barrier against a lateral migration.

Figure 10:
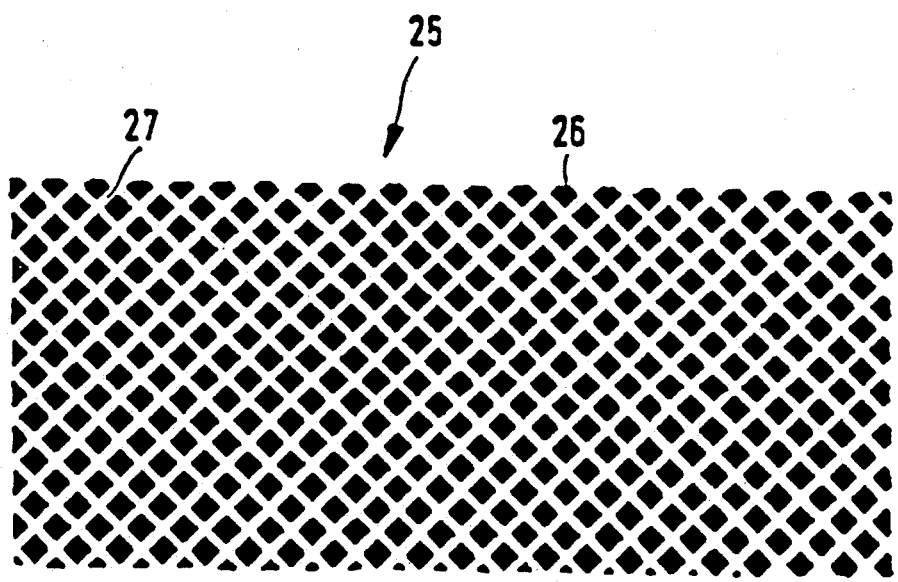
FIG. 10 illustrates a topview of the surface of the peelable protective film to be placed onto the skin-compatible adhesive layer of the device.

As shown in the FIG. 2, 4, 6, 7, 8 and 10, a peelable polyester film (4, 16, 24) is placed on the skin-compatible adhesive layer (3) (see FIG. 2 and 4) and (10), respectively (see FIG. 6 and 7), and (19), (see FIG. 8) respectively, covering the reservoir (5, 11, 22) of the device at the delivery side in the storage state, whereby this peelable polyester film is coated at the side (25) facing the skin-compatible adhesive layer, with a suitable pattern of a silicone or of another adhesion releasing material and whereby the remaining non-siliconized or non-coated protective film surface will undergo an intimate adhesive bond with the adhesive layer (19), thereby forming a reliable barrier against a lateral migration of the micro-emulsion. As seen in FIG. 10, the coated part-areas (26) of the pattern, which may also be seen as islands, are uniformly formed as squares separated by non-coated stays (27) of an equal width.

However, the partial areas or islands of the pattern, respectively, may also have a circular, triangular, rectangular, elliptic, rhombic shape or the like, whereby the various geometric shapes of the partial areas (26) determine an accordingly shaping of the stays (27). For instance, if the partial areas have a circular shape, narrow stays (27) are formed between the closest adjacent edges of the circles, while the crossing areas of the stays are accordingly widened. The particular geometric shaping of the part-areas (26) and of the respective stays (27) depends on the various requirements to be met by the peelable polyester film (4, 16, 24), dealing with the offsetting demands, namely the adhesive strength on the one hand and the easy peelability or removability of the polyester film (4, 16, 24) on the other hand, as needed for the particular application case as a protective film of the bandage strip.

EXAMPLE 3

A device according to the invention for administering a micro-emulsion containing active ingredients, was prepared as follows:

A copolymer of iso-octyl acrylate and acrylamide (93:7) was dissolved in a mixture of ethyl acetate and methanol (15:1). The concentration of the copolymer in the adhesive solution is to be 15 to 30%.

The adhesive solution was spread in a suitable manner on the one side of an adhesion-release treated paper. After the spreading, the adhesive layer was dried at first at room temperature for 15 minutes and, then, at 60° C. in a circulating hot air oven for 90 minutes. The coating weight of the dried adhesive is to be 150 to 300 g/m².

The adhesive was laminated onto a closed cell polyethylene foam piece, which had been coated at the other side with a hot-melt adhesive of ethylene/vinyl acetate. Then, holes were punched into the laminate having a suitable diameter of e.g. 30 mm.

A suitable polyethylene film vapor-coated with aluminum was heat-sealed with the hot-melt adhesive layer. Then, pieces of a non-woven fleece of viscose-rayon, surface-treated with polyolefins, were placed into the punched out openings.

The pieces of the non-woven fleece were saturated with the micro-emulsion containing the active ingredients. Subsequently, the one-sided adhesion-release treated paper was removed. Then, a protective polyester film coated with a pattern of an adhesion-release agent applied in squares with an edge length of 3 mm and with a stay width between the squares of 0.5 mm was laminated onto the pressure-sensitive adhesive layer.

Then, the laminate was cut into individual pieces of a suitable size of, e.g., 50×60 mm.

| | LEGEND |
|---|---|
| 1 | Polymer film |
| 2 | Foamed material piece |
| 3 | Adhesive layer |
| 3a | Adhesive |
| 4 | Protective paper liner |
| 5 | Reservoir (supply) |
| 6 | Pull-off strap |
| 7 | Adhesive layer, high strength |
| 8 | Adhesive layer, repeatedly usable |
| 9 | Non-woven fleece tape |
| 10 | Adhesive |
| 11 | Absorbent material piece (absorbent disk) |
| 12 | Filling opening |
| 13 | Adhesive layer, repeatedly usable |
| 14 | Pull-off strap |
| 15 | Cover |
| 16 | Protective film (liner) |
| 17 | Non-transparent barrier layer |
| 18 | Polyethylene foam piece |
| 19 | Adhesive layer |
| 20 | Hot-melt adhesive layer |
| 21 | Reservoir |
| 22 | Material piece of an absorbent material |
| 23 | Protective polyethylene film |
| 24 | Protective film (polyester) |
| 25 | Surface (of the polyester film 24) |
| 26 | Part-areas |
| 27 | Stays |

What is claimed is:

1. A device for a dermal administration of a drug to a patient, comprising:
 a reservoir, said reservoir having an opening for delivering the drug onto the skin of the patient and an inlet for receiving the drug, and
 a carrier element for carrying the reservoir, said carrier element having a skin-compatible adhesive layer on one side thereof, said device further comprising a peelable protective liner covering the adhesive layer and the opening of the reservoir, wherein the carrier element is formed by a relatively flat foamed material piece with closed pores and is traversed by a punched out hole extending between the opposite surface and having walls defining the reservoir, and wherein a polymer film coated with an adhesive is placed onto the surface of the carrier element opposite the side carrying the skin-compatible adhesive layer thereby covering the inlet of the reservoir, and wherein the peelable protective liner is coated with a pattern of adhesion releasing materials at the side facing the adhesive layer in such a way that a barrier is formed by the remaining non-coated protective film surface in conjunction with the adhesive layer to prevent a lateral migration of the drug preparation into the skin-compatible adhesive layer.

2. A device according to claim 1, wherein the punches out perforating holes have a circular cross-section and are peripherally bordered at the delivery side by the adhesive layer.

3. A device according to one of the claims 1 or 2, wherein the protective film and the polymer film are each provided with a pull-off strap extending beyond the surface of the foamed material piece.

4. A device according to one of the claims 1 to 3, wherein the polymer film is non-transparent and fastened to the foamed material piece by means of two parallel adhesive strips and aligned along the crosswise edges, whereby the adhesive strip situated a distance away from the pull-off strap of the polymer film is formed by an adhesive with a high adhesive strength and the adhesive strip adjacent to the pull-off strap is formed by a repeatedly usable adhesive of a low adhesive strength.

5. A device according to one of the claims 1 to 4, wherein the polymer film is transparent and micro-perforated.

6. A device according to one of the claims 1 to 5, wherein the coated and non-coated partial areas and of the pattern on the surface of the peelable protective film in contact with the adhesive layer are varied in their sizes and/or in the ratio of their geometrical shapes according to the consistency of the drug preparation for optimizing the barrier effect of the uncoated partial areas and the peelability of the protective film.

7. A device according to one of the claims 1 to 5 and 6, wherein the coated partial areas of the pattern are squares separated by non-coated stays.

8. A device according to one of the claims 1 to 5, 6 and 7, wherein the coated partial areas of the pattern have a circular, triangular, rectangular, elliptic or rhombic shape and the intermediary non-coated partial areas have a correspondingly geometric shape.

9. A device according to one of the claims 5, 6 and 8, wherein the coated partial form islands and the non-coated stays form a continuous barrier.

10. A device according to one of the claims 5, 6, 7, 8 and 9, wherein the skin-compatible adhesive consists of components, which prevent a penetration by the drug formulation.

* * * * *

UNITED STATES PATENT AND TRADEMARK OFFICE
CERTIFICATE OF CORRECTION

PATENT NO. : 5,244,677
DATED : September 14, 1993
INVENTOR(S) : Kreckel et al.

It is certified that error appears in the above-indentified patent and that said Letters Patent is hereby corrected as shown below:

Col. 10, lines 14-15, "claims 1 to 5 and 6" should read --claims 1 to 6--.

Col. 10, lines 17-18, "claims 1 to 5, 6 and 7" should read --claims 1 to 7--.

Col. 10, line 22, "claims 5, 6 and 8" should read --claims 1 to 8--.

Col. 10, line 23, after "partial" insert --areas--.

Col. 10, lines 25-26, "claims 5, 6, 7, 8 and 9" should read --claims 1 to 9--.

Signed and Sealed this

Thirty-first Day of January, 1995

Attest:

BRUCE LEHMAN

Attesting Officer

Commissioner of Patents and Trademarks